United States Patent [19]
Goodenough et al.

[11] Patent Number: 5,165,050
[45] Date of Patent: Nov. 17, 1992

[54] SPHERICAL TEST BODY FOR AN IMAGE RECONSTRUCTING APPARATUS

[75] Inventors: David J. Goodenough, Myersville, Md.; Joshua R. Levy, Salem, N.Y.

[73] Assignee: The Phantom Laboratory, Incorporated, Salem, N.Y.

[21] Appl. No.: 616,604

[22] Filed: Nov. 21, 1990

[51] Int. Cl.[5] .............................................. G01R 33/20
[52] U.S. Cl. ..................................... 324/318; 324/322
[58] Field of Search ............... 324/300, 307, 309, 318, 324/322; 340/572; 273/110

[56] References Cited

U.S. PATENT DOCUMENTS

| | | | |
|---|---|---|---|
| 3,310,885 | 3/1967 | Alderson | 35/17 |
| 4,055,771 | 10/1977 | Goodenough et al. | 250/505 |
| 4,126,789 | 11/1978 | Vogl et al. | 250/505 |
| 4,296,329 | 10/1981 | Mirabella | 250/491 |
| 4,344,183 | 8/1982 | Jacobson | 378/207 |
| 4,451,038 | 5/1984 | Nagy | 273/110 |
| 4,551,678 | 11/1985 | Morgan et al. | 324/300 |
| 4,613,754 | 9/1986 | Vinegar et al. | 250/252.1 |
| 4,613,819 | 9/1986 | Chui | 324/318 |
| 4,618,826 | 10/1986 | Smith et al. | 324/308 |
| 4,625,168 | 11/1986 | Meyer et al. | 324/300 |
| 4,644,276 | 2/1987 | Sierocuk et al. | 324/307 |
| 4,692,704 | 9/1987 | Gray | 324/318 |
| 4,712,094 | 12/1987 | Bolson Sr. | 340/572 |
| 4,777,442 | 10/1988 | Rosenthal | 324/318 |
| 4,782,502 | 11/1988 | Schulz | 378/18 |
| 4,816,762 | 3/1989 | Bohning | 324/318 |
| 4,818,943 | 4/1989 | Chandra | 324/318 |
| 4,870,666 | 9/1989 | Lonn et al. | 378/18 |
| 4,873,707 | 10/1989 | Robertson | 378/18 |
| 4,888,555 | 12/1989 | Vaughan et al. | 324/318 |

*Primary Examiner*—Michael J. Tokar
*Attorney, Agent, or Firm*—Heslin & Rothenberg

[57] ABSTRACT

The subject invention provides a spherical test body for determining the operating characteristics of an image reconstructing apparatus comprising a hollow spherical first housing positionable within the apparatus, a second housing, means for positioning the second housing within the spherical first housing, and means for determining the operating characteristics, the latter means positioned within the second housing. The spherical test body of the subject invention can be used to determine the operating characteristics of any apparatus which reconstructs an image of the interior of a human across a plane at any angle.

31 Claims, 9 Drawing Sheets

SPHERICAL TEST BODY FOR AN IMAGE RECONSTRUCTING APPARATUS

FIELD OF THE INVENTION

This invention relates to equipment used to reconstruct an image of the interior of a subject across a plane. The invention relates more particularly to a means for testing the operating characteristics of such equipment and a method for such testing.

BACKGROUND OF THE INVENTION

Numerous types of medical equipment, as is well known, are used to reconstruct an image of the interior of a subject across a plane. Examples of such medical equipment include x-ray tomographic scanners, magnetic resonance imaging scanners, and nuclear medicine emission computed tomography (ECT) scanners. Each of these scanners are used to reconstruct an image of a cross section, or slice, through a patient's body. Consecutive cross sectional images are then combined to create an image of the interior of a subject.

Tomography is a medical technique of radiographic analysis which provides an image of a particular plane of a body under examination. In one form of tomographic instrument known as a CAT scanner (computed axial tomography), an x-ray source and x-ray detectors are positioned in alignment on opposite sides of a subject under examination and simultaneously scan an edge of a cross sectional plane or slice of finite thickness extending through the subject.

Intensity of x-ray transmission through the subject is determined by sampling an electrical output of the detectors. Sampling occurs in numerous locations in the direction of a single scan. The x-ray source is then rotated a predetermined angular distance about an axis normal to the plane or slice through the subject and another scanning of the edge in a different direction is obtained. Resultant data is processed by a computer to reconstruct an image of the planer cross-section or slice through the patient's body.

In another form of image reconstruction known as magnetic resonance imaging (MRI), the body of a subject is placed within a magnetic field. When a radio-frequency at the resonance (Larmor) frequency is applied to the subject within the magnetic field, the magnetic moment of the subject's atoms which are normally in random alignment align in a north and south direction relative to the magnetic field. When the radiofrequency is terminated, the atoms return to their random alignment and in so returning will emit energy via radiofrequency at the same resonance frequency. This radiofrequency is detected via an antenna and the resultant data generated by the detection can be analyzed into contributing frequencies and processed by a computer to reconstruct an image in cross section of the patient's body. This form of image reconstruction is also known as nuclear magnetic resonance (NMR) imaging.

Image reconstructing apparatus include such CAT scanners, MRI or NMR scanners, ECT scanners, and any apparatus that receives data and processes it to create an image in cross section of the patient's body.

It is desirable at times to verify that the operation of an instrument for reconstructing an image of the interior of a subject conforms with its known capabilities. In addition, it is desirable to predetermine the capabilities of the instrument for the performance of specific examinations.

A test body (phantom) for determining the operating characteristics of a scanning tomographic analytical apparatus of the type known as a CAT scanner is disclosed in co-assigned Goodenough et al. U.S. Pat. No. 4,055,771, issued Oct. 25, 1977. The contents of this U.S. Patent in its entirety are hereby incorporated into this application in order to more fully define the state of the art to which the subject invention pertains. The test body comprises energy absorption means arranged in layered arrays extending generally parallel to a direction of projection of the x-ray beam, and means for positioning the energy absorbing means between a scanning x-ray beam and a transmission intensity detector of the tomographic apparatus.

A phantom for determining the operating characteristics of a nuclear magnetic resonance scanner is disclosed in Newman and Sierocuk U.S. Pat. No. 4,644,276, issued Feb. 17, 1987. The phantom comprises at least two test plates which include means for testing parameters of the scanner and allows the scanner to be tested in the plane in which these test plates lie.

Another phantom for determining the operating characteristics of a magnetic resonance imaging scanner is disclosed in Gray U.S. Pat. No. 4,692,704, issued Sep. 8, 1987. The phantom includes a generally tubular body containing a cylindrical stack of a plurality of leaves. Each leaf has one or more wedge shaped slices or sectors cut out for identification and reference purposes.

CAT scanners reconstruct images in fixed planes. Magnetic resonance imaging systems are not mechanically dependent in the way that CAT scanner systems are, therefore magnetic resonance imaging scanners are able to reconstruct images in any plane. A cylindrical phantom, used for testing the performance of a CAT scanner and some MRI scanners, does not provide for this capability. Therefore, the subject invention provides a spherical phantom which can measure the performance of a magnetic resonance imaging scanner (or a CAT scanner) in more than fixed planes, whereas previous phantoms have only allowed imaging in up to three test planes, X, Y and Z, mounted in a cylindrical housing. The spherical phantom of the subject invention is filled with a liquid and by inserting the test objects used in the subject invention into the liquid filled sphere, which can be rotated in all directions, variable plane positioning can be obtained.

In addition to providing multiple plane measurements, the spherical phantom of the subject invention eliminates some artifacts created by the hard corners found in cubical and cylindrical phantoms.

In addition to the imaging features provided by the subject spherical phantom, problems associated with many liquid filled phantoms involving the removal of numerous screws to open the phantoms are solved by providing a threaded joint which allows the phantom to be opened without tools. By providing a sealing means, such as an 0-ring, the seal between the two halves of the spherical phantom prevents leakage which is also a common problem with liquid filled phantoms.

Additionally, a small insert is glued or cast into the sphere to allow for longer threads to be cut through the sphere surface, preventing potential leaking problems with filling ports on the thin surface of the sphere and forming a solid base for an internal mounting post and/or a plug.

These problems associated with previous phantoms are also encountered in phantoms used to test other medical equipment used to reconstruct an image of the interior of a subject across a plane. Thus, there continues to be a need for a test body (phantom) for determining the operating characteristics of imaging equipment. These test bodies must provide for the efficient and accurate verification of the operating characteristics of the equipment.

SUMMARY OF THE INVENTION

Accordingly, it is an object of the subject invention to provide an improved means for testing the operation of an image reconstructing instrument. Another object of the invention is to provide an improved phantom for verifying operating characteristics of an image reconstructing instrument.

More specifically, it is an object of the invention to provide a spherical phantom having means for verifying a plurality of operating characteristics of an image reconstructing instrument.

A further object of the invention is to provide such a spherical phantom for verifying a plurality of operating characteristics of an image reconstructing instrument used to scan a subject at any angle.

It is a further object of the subject invention to provide a spherical phantom which eliminates some artifacts created by the hard corners found in cubical and cylindrical phantoms. It is an additional object of the subject invention to provide such a spherical phantom which can be filled with liquid and sealed with a threaded joint and a sealing means, which can be easily opened without tools. It is a further object of the subject invention to provide such a liquid filled phantom which does not leak. It is an object of the subject invention to provide a spherical phantom which allows longer threads to be cut through the sphere surface preventing leaking problems and forming a solid base for an internal mounting post and/or a plug.

In accordance with the features of this invention, a spherical test body is provided for determining an operating characteristic of an apparatus used to reconstruct an image of the interior of a subject across a plane, the spherical test body comprising a hollow spherical first housing positionable within the apparatus and a plurality of means for determining the operating characteristics, the plurality of means positioned within the first housing. In one embodiment, the spherical test body further comprises a second housing and means for positioning the second housing within the spherical first housing, wherein the plurality of means are positioned within the second housing.

The spherical test body, when scanned by the apparatus, produces data which is processed by a computer to reconstruct an image of the subject as a cross-sectional image or as a three dimensional image. The image thus produced is compared to a predetermined image created by the spherical test body to determine or to verify the operating characteristics of the apparatus being tested.

In accordance with more particular features of the subject invention, one embodiment provides a spherical test body wherein the hollow spherical first housing comprises a first half and a second half, and a means for connecting the first and the second halves. The spherical test body additionally comprises a second housing which, in one embodiment, comprises a cube having four walls, a top surface, and a bottom surface. The means for determining the operating characteristics of the apparatus are positioned within the cube.

Scanning of the spherical test body with the apparatus provides images which when compared to predetermined images enable determination of particular characteristics of the apparatus. Such characteristics include, but are not limited to, detection by the apparatus of small objects at various contrast levels, detection by the apparatus of small lesion-like masses in a surrounding matrix, detection of small objects of varying sizes and contrasts, fidelity of a reconstructed image with respect to overlaps and voids between adjacent scans, resolution of the apparatus at various contrast levels, the generation of the data for the determination of the modulation transfer function, the capability of the apparatus to distinguish between materials of different contrasts which do not have sharply defined edges, the capability of the apparatus to discriminate between materials of different densities or other physical characteristics such as T1 and T2, the capability of the apparatus to determine the centering of rotation of the apparatus, the capability of the apparatus to produce spatially uniform scans, and the capability of determining the slice thickness.

BRIEF DESCRIPTION OF THE DRAWINGS

These and other objects, features, and advantages of the subject invention will be evident from the following detailed description when read in conjunction with the accompanying drawings in which:

FIG. 9b is a side elevational view of the stand shown in FIG. 9a.

DETAILED DESCRIPTION OF THE INVENTION

As indicated hereinbefore, it is desirable at times to determine and to verify the operating characteristics of an image reconstructing apparatus. A spherical test body (10) is provided in accordance with the subject invention, which when scanned by a properly operating image reconstructing apparatus, causes the apparatus to reconstruct an image having a predetermined pattern. This known pattern is compared with an actual pattern generated when the spherical test body is scanned by an image reconstructing apparatus being tested for determining and verifying the operating characteristics of the latter apparatus.

Figure 1:
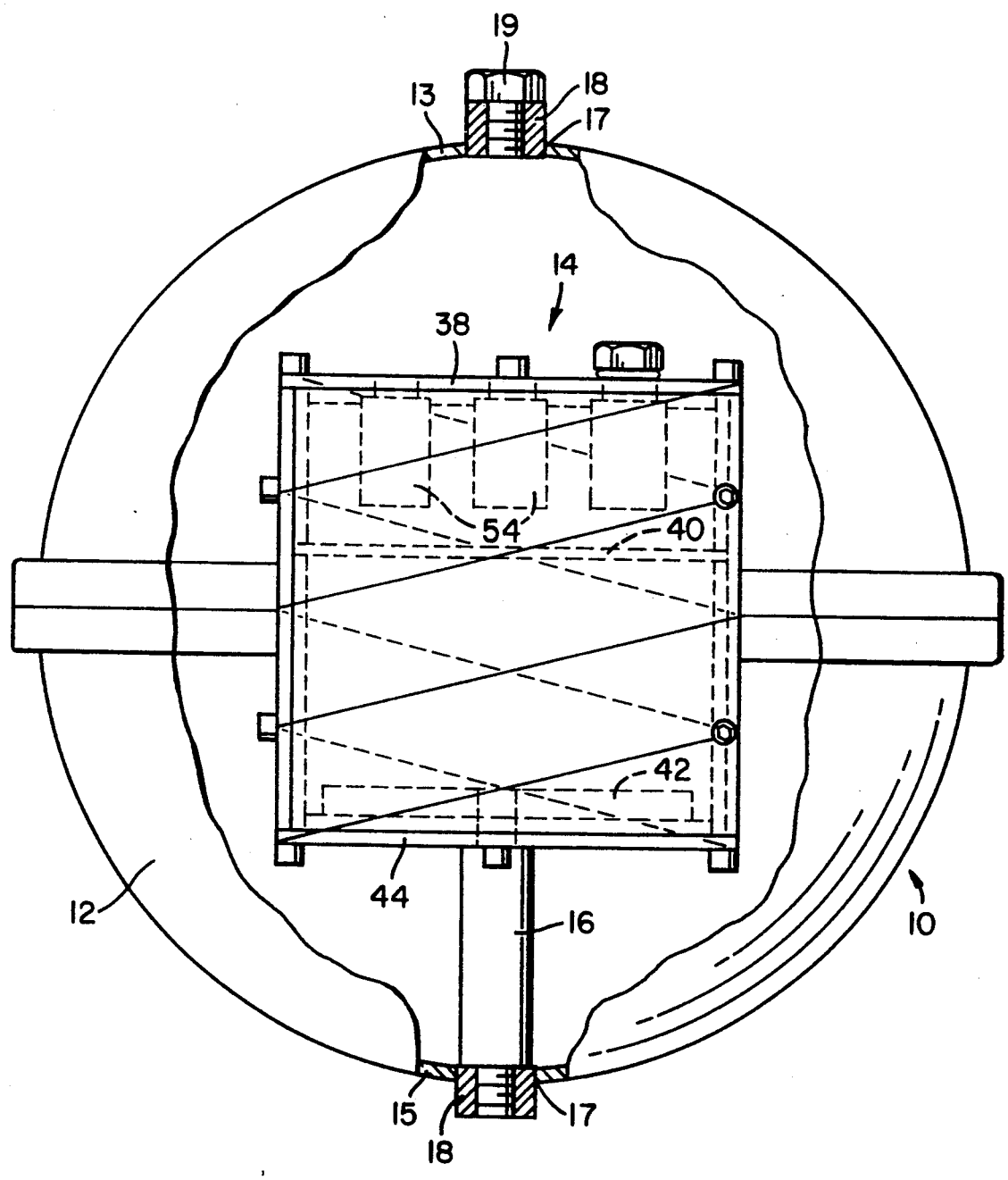
FIG. 1 is a side elevational view of one embodiment of the spherical test body of the subject invention.

The test body (see FIG. 1) comprises a hollow spherical first housing (12) positionable within the apparatus, and a cube (14) positioned within the hollow spherical housing, the cube containing the test objects (40, 42, 50, 54) for determining the operating characteristics of the apparatus.

In a preferred embodiment of the subject invention, the test objects within the cube include test objects for a sensitometry assay (54), a resolution plate (40), and a low contrast plate (42).

Figure 2:
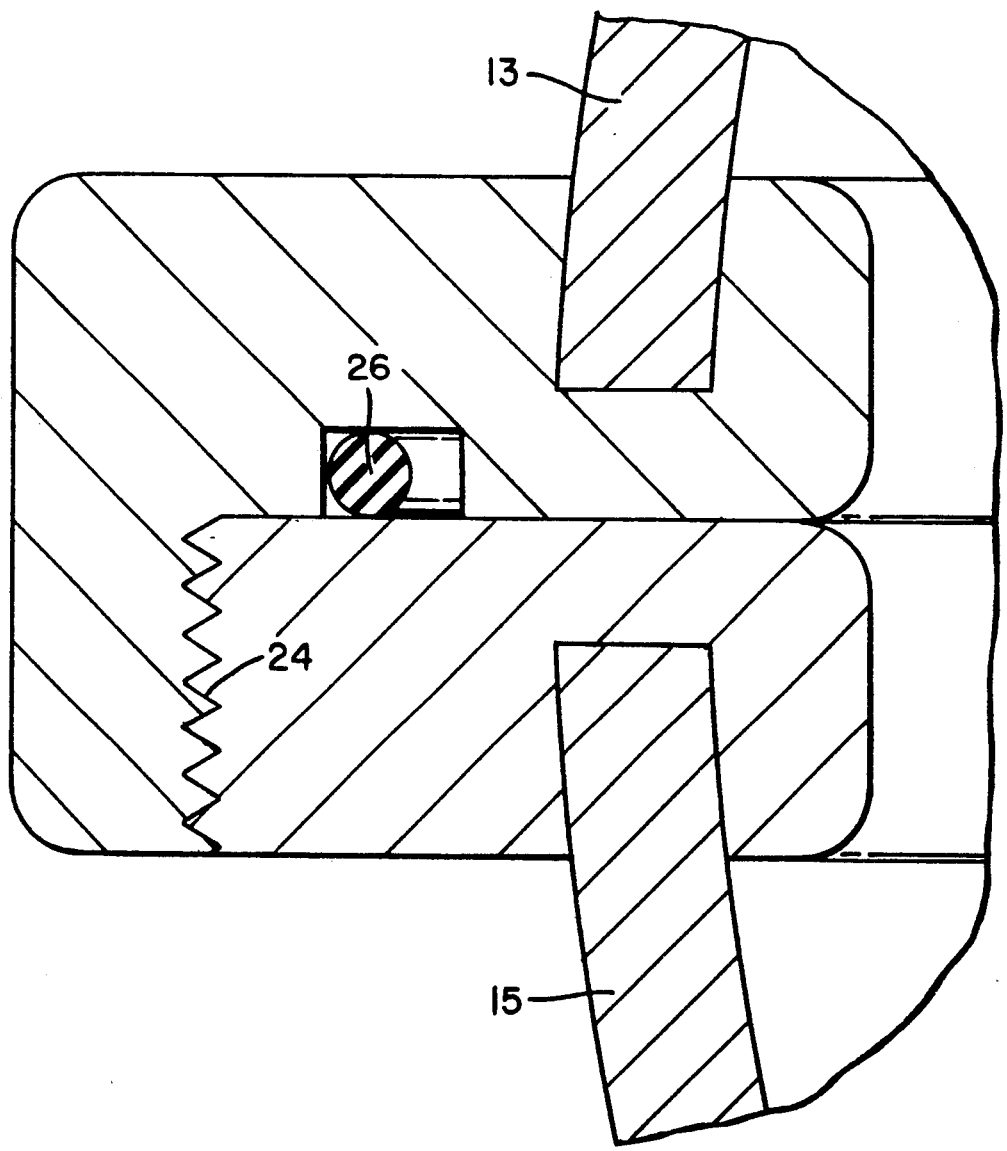
FIG. 2 is a cross-sectional view of the connection of the two halves of the hollow spherical housing shown in FIG. 1.

The hollow spherical housing (12), which comprises the outer portion of the spherical test body (10), comprises a first half (13) and a second half (15). The halves are joined (see FIG. 2) so as to create a spherical test body by utilizing threaded grooves (24). These threaded grooves (24) are positioned along the exterior of the hollow spherical housing so as to produce a minimum indentation on the interior surface of the spherical housing.

An O-ring (26) is positioned within the threadable grooves (24) so as to provide a watertight seal when the two halves (13,15) of the spherical housing are threaded together. At each end of the spherical housing an aperture (17) is located (see FIG. 1). Aligned with this aperture is a member (18) having a threaded central core. By utilizing such a member (18), these apertures (17) in the spherical housing can be tightly sealed so as to prevent leakage of fluid from the spherical housing. The central core of the top member is sealed using a bolt (19) which is threaded into the central core. The central core of the lower threaded member is sealed using a rod (16) which is threaded into the member. The interior portion of the rod is also threaded and protrudes towards the center of the spherical housing. This interior end of the threaded rod (16) will be used to position the cube (14) containing the test objects (40, 42, 50, 54) within the spherical test body (10).

The aperture (17) located on the top of the spherical test body can be used to easily and conveniently remove fluid from the spherical test body by simply removing the bolt (19), without the need for separating the two halves of the test body. The construction of the spherical housing provides for the easy opening and closing of the test body by merely threading and unthreading the two halves.

Figure 3:
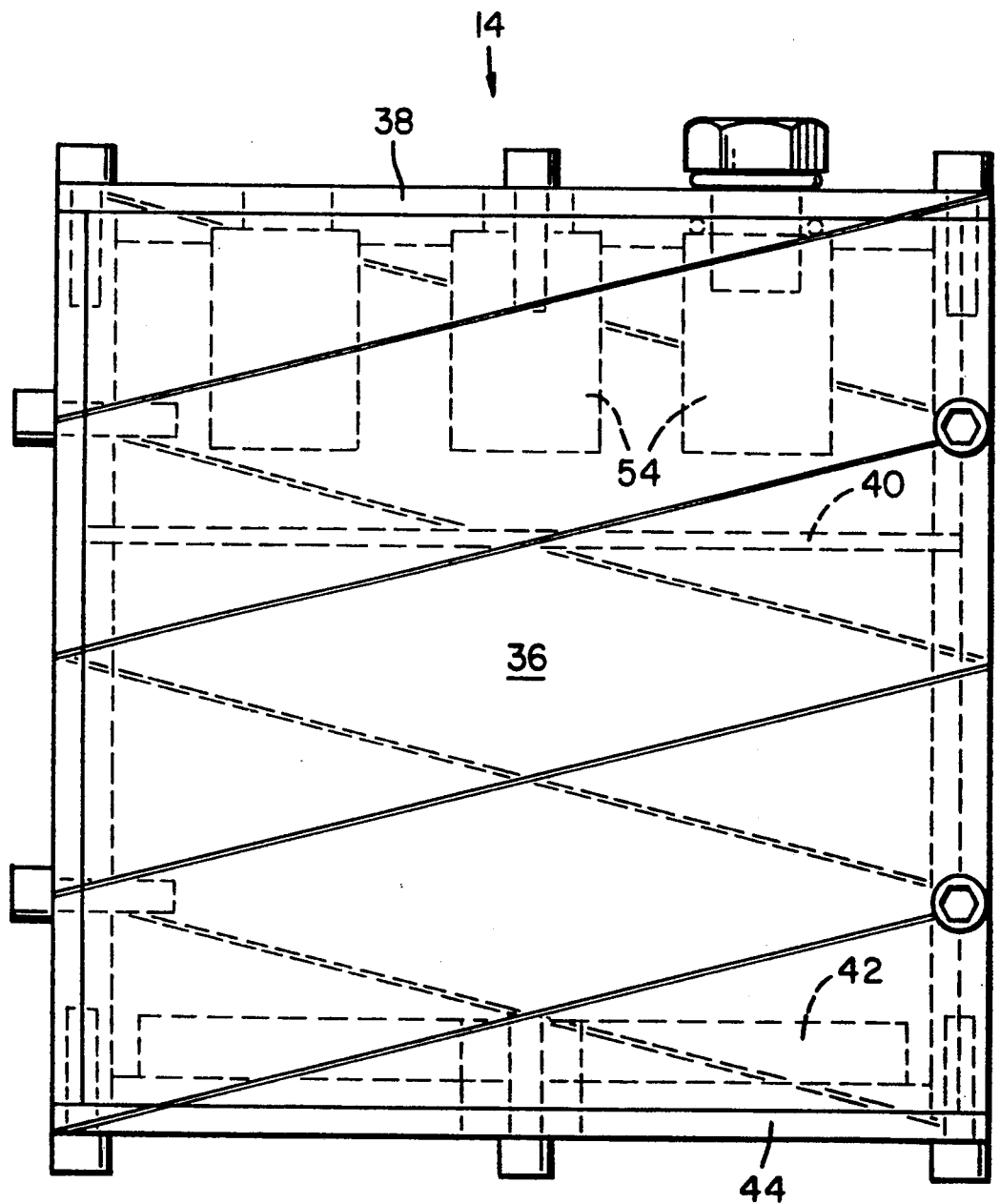
FIG. 3 is a side elevational view of the test cube and test, objects shown in FIG. 1.

FIG. 3 illustrates the test cube (14) used in the subject invention. The test cube comprises four sides (36), a top (38) and a bottom (44). The threaded rod (16) is connected to the test cube (14) at a threaded aperture (60) in the bottom surface (44).

Figure 5:
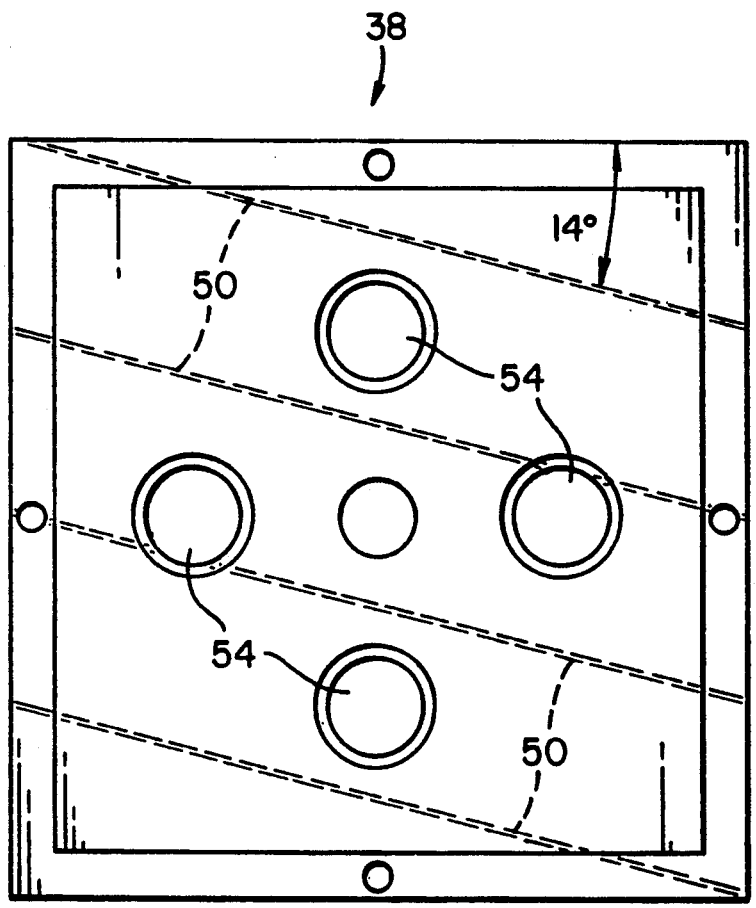
FIG. 5 is a bottom view of the test cube top shown in FIG 3.

Located within the cube are the means for determining the operating characteristics of the apparatus being tested which comprise test objects. At least one of the test objects is adapted for testing the capability of the apparatus to differentiate between objects at different contrast levels. In one embodiment (see FIGS. 3 and 5), the test objects comprise one or more test element bodies (54) formed of material having a predetermined energy absorption characteristic based on physical characteristics, such as density, T1 and T2. The test element bodies (54) have different absorption characteristics and comprise cylinder shaped bodies.

Figure 7:
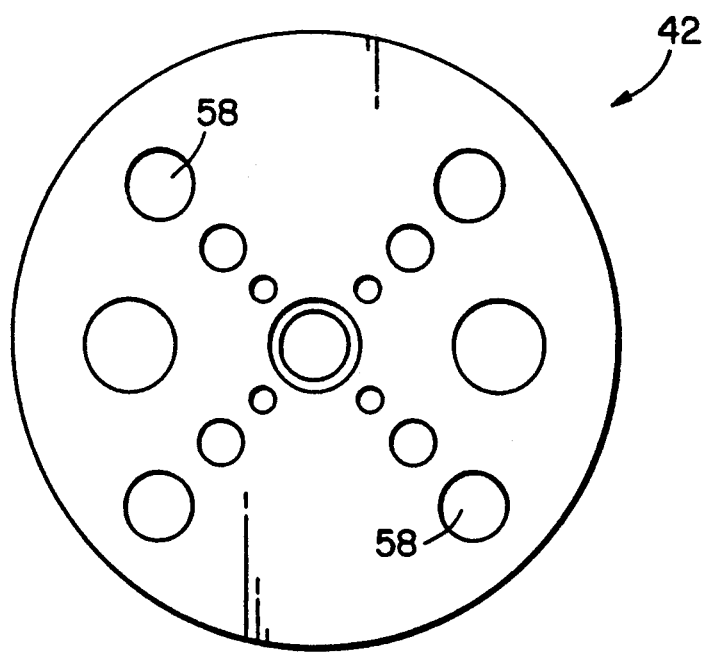
FIG. 7 is a top view of the low contrast plate shown in FIG. 3.

At least one of the test objects is adapted for testing volume contrast sensitivity of the apparatus. These test objects (see FIG. 7) comprise a plurality of voids (58) positioned within the plates. The internally positioned voids (58) are cylinder shaped and have differing diameters and depths. Through volume averaging, these voids when filled with a consistent solution will have differing energy absorption characteristics based on physical characteristics. The test bodies have outside diameters progressively increasing in size such as 0.40 centimeters, 0.60 centimeters, and 1.00 centimeters. These cylindrical shaped bodies also have progressively increasing depths such as 0.05 centimeters, 0.075 centimeters, 0.10 centimeters, and 0.20 centimeters.

Figure 4:
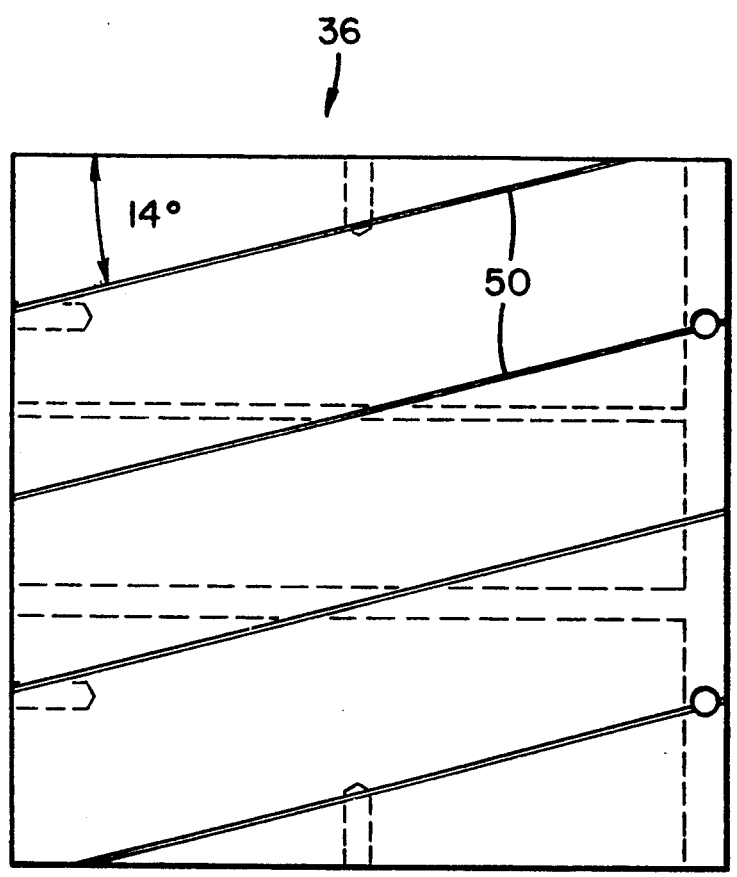
FIG. 4 is a side elevational view of the test cube side plate shown in FIG. 3.
Figure 8:
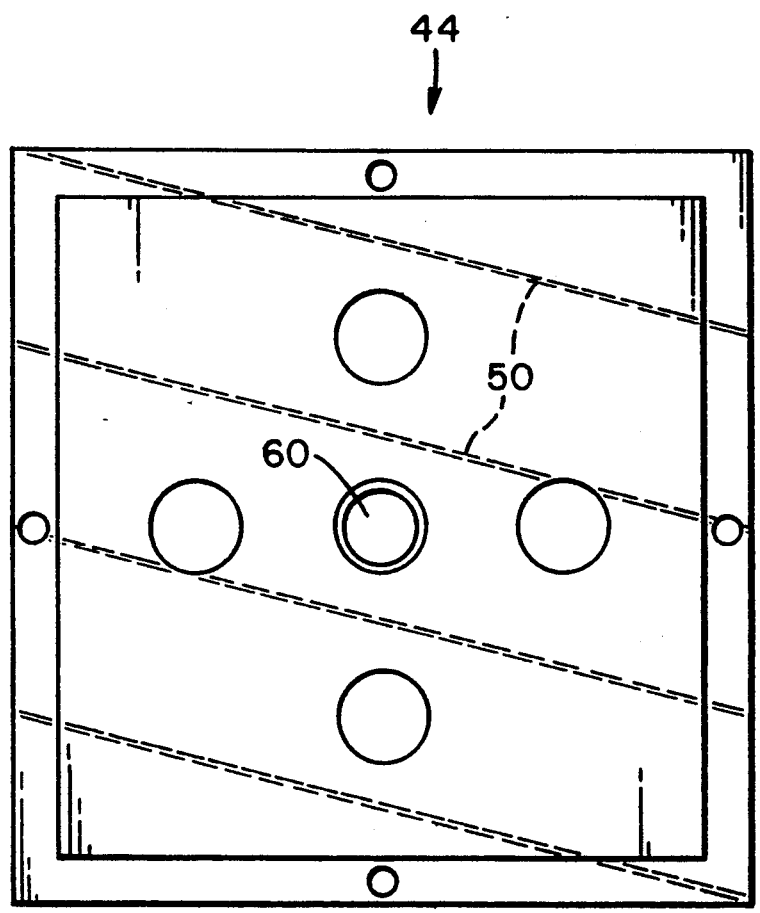
FIG. 8 is a top view of the test cube bottom shown in FIG. 3.

At least one of the test objects is adapted to detect fidelity of the apparatus in reconstructing an image. These test objects comprise channels (50) located on the outer surface of the cube. These channels (50) are placed diagonally in a continuous pattern around the sides (36) of the cube (see FIG. 4), and also diagonally across the top (38) (see FIG. 5) and bottom 44) (see FIG. 8) portions of the cube. The channels located on the sides of the cube are adapted to test the fidelity of the reconstructed image within a slice. In this regard voids or information missing from the reconstructed image is detected. In addition these channels are adapted to test for overlaps of the scanner between adjacent slices, which may occur in the reconstructed image. These channels are preferably 0.02 centimeters deep and 1 centimeter wide and are placed at 14° angles.

At least one of the test objects is adapted for testing the capability of the apparatus to distinguish between relatively small objects of differing sizes and contrasts. These test objects (see FIG. 7) comprise a plurality of bodies or voids (58) positioned within the plate. These internally positioned bodies or voids (58) are cylinder shaped, have differing diameters and depths, and have energy absorption characteristics based on physical characteristics. These test objects are also adapted for testing volume contrast sensitivity of the apparatus.

At least one of the test objects is adapted for testing the resolution of the apparatus. The test object (see FIG. 6) comprises line pairs (56), the line pairs being of predetermined width. The number of line pairs per unit length varies in the direction of scoring. These line pairs are provided in the form of a high resolution gauge.

Figure 6:
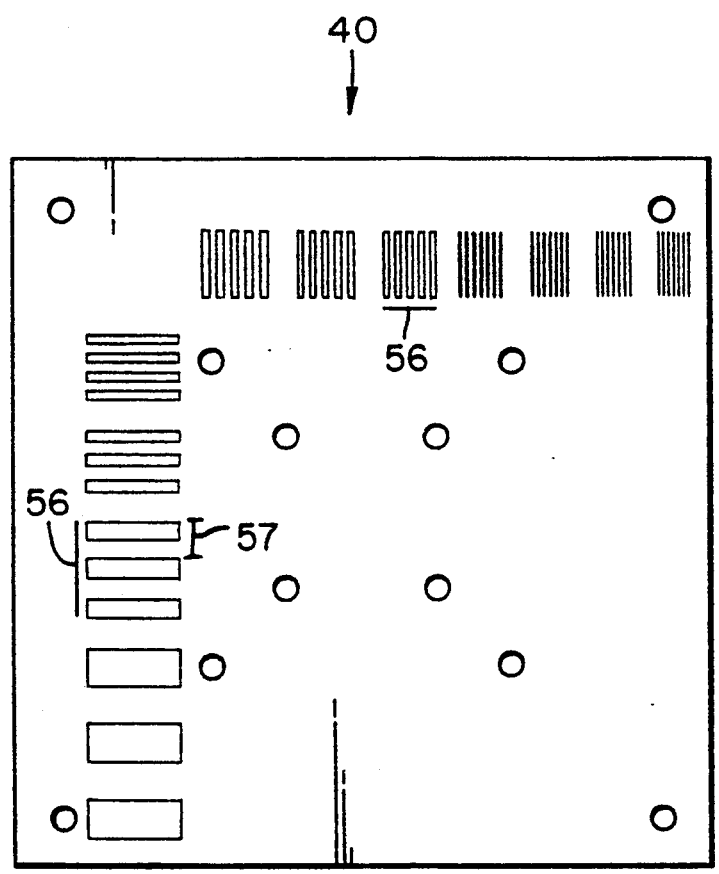
FIG. 6 is a top view of the high resolution plate shown in FIG. 3.

Line pairs (56), referring to FIG. 6, are defined based on the width of a space and a "tooth" on the resolution gauge. One line pair (57) comprises the space and the tooth. Twenty line pairs per centimeter indicates that twenty of these line pairs (57) can be cut in a one centimeter distance. Slot width on the resolution gauge indicates the width of a slot, i.e. the width of a space between teeth. Each tooth is generally the same width as its adjacent slot width.

The direction of scoring of the resolution gauge, referring again to FIG. 6, means that the line pair per unit length varies as you move along the gauge. For example, the direction of scoring proceeds from slot widths 0.197 to 0.098 to 0.065, etc. On the perpendicular side of the resolution gauge, the direction of scoring proceeds, for example, from slot widths 0.0394 to 0.0328 to 0.0281, etc. These varying slot widths produce line pairs of varying sizes.

One of the test objects of the subject invention may be adapted for testing the modulation transfer function of the apparatus. The test objects generate data for the calculation of the square wave response function. The test object may also comprise a spherical bead, such as a tungsten carbide bead, for calculation of the point spread function. The spherical bead is described in detail in a co-assigned U.S. patent application filed concurrently with the subject application, entitled "Test Body and Element For A Scanning Image Reconstructing Apparatus".

The various test bodies described are selected to provide predetermined physical characteristics which test the operating characteristics of the apparatus. While various materials and configurations may be selected to suit the various testing requirements of the apparatus, the materials given as examples provide for the desired testing of the indicated characteristics of the test objects.

The hollow spherical housing is formed from any plastic, one such suitable plastic being acrylic. The housing may also be cast from a suitable plastic, such as urethane or epoxy. The cube is also made from any plastic, one such suitable plastic being acrylic.

The spherical test body of the subject invention is filled with a fluid, such as copper sulfate, which is commonly used for MRI. Other fluids which can be utilized in the process of the subject invention are well known to those skilled in the art. Fluids which can be utilized with equipment other than MRI are also well known to those skilled in the art.

A specimen can be placed within the spherical housing so as to contain and position the specimen within the fluid chamber during scanning.

Figure 9B:
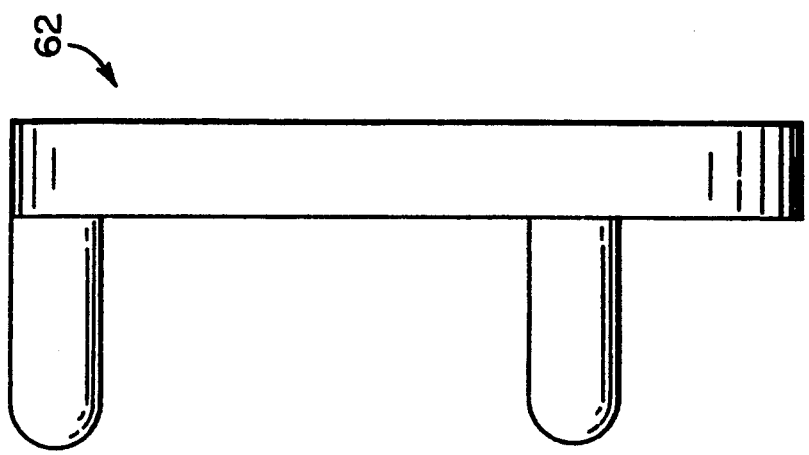
Figure 9A:
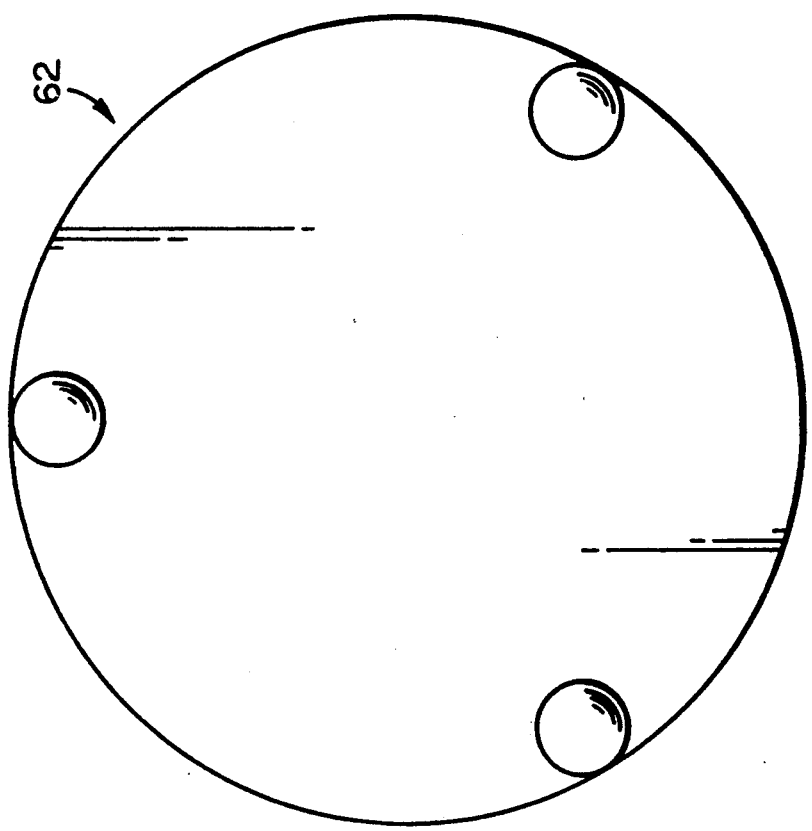
FIG. 9a is a top view of a stand which is one embodiment of a means for positioning the subject invention within an apparatus.

The spherical test body can be positioned within the image reconstructing apparatus utilizing a stand, such as that shown in FIGS. 9a and 9b. The stand comprises a circular base from which three fingers protrude. The sphere is placed upon the three fingers. FIG. 9b shows the protrusion of two of the fingers from the base portion.

Although a preferred embodiment has been depicted and described in detail herein, it will be apparent to those skilled in the relevant art that various modifications, additions, substitutions and the like can be made without departing from the spirit of the invention, and these are therefore considered to be within the scope of the invention as defined by the following claims.

What is claimed is:

1. A spherical test body for determining an operating characteristic of an apparatus used to reconstruct an image of the interior of a subject across a plane, said spherical test body comprising:
   a hollow spherical first housing positionable within said apparatus, said hollow spherical first housing including a first half and a second half and means for connecting said first and said second halves, wherein said hollow spherical first housing has one or more apertures therein;
   a second housing;
   means for positioning said second housing within said hollow spherical first housing;
   a plurality of means for determining said operating characteristics, said plurality of means positioned within said second housing; and
   a member attachable to an outside surface of said spherical first housing, said member having a threaded central core, wherein when said member is attached to said outside surface of said spherical first housing, said threaded central core aligns with one of said apertures in said spherical first housing.

2. The spherical test body of claim 1, wherein said means for connecting said first and said second halves comprises grooves on each of said halves, said grooves of said first half threadable with said grooves of said second half, wherein when said grooves of said halves are threaded together, a sphere is formed.

3. The spherical test body of claim 2 further comprising means for sealing said first half to said second half.

4. The spherical test body of claim 3, wherein said means for sealing said first and said second halves comprises an O-ring insertable within said groove so as to form a seal.

5. The spherical test body of claim 1 further comprising a bolt threadable into said member.

6. The spherical test body of claim 1 further comprising a rod, one end of said rod threadable into said member, wherein when said end of said rod is threaded into said member, the other end of said rod protrudes toward the center of said spherical first housing.

7. The spherical test body of claim 6, wherein said rod comprises said means for positioning said second housing within said spherical first housing.

8. The spherical test body of claim 7, wherein said second housing comprises a cube having four walls, a top surface, and a bottom surface.

9. The spherical test body of claim 8, wherein said cube has a threaded aperture therein.

10. The spherical test body of claim 9, wherein said means for positioning said cube within said spherical first housing comprises said rod, said other end of said rod threadable into said aperture in said cube.

11. The spherical test body of claim 1, wherein said means for determining said operating characteristics comprise test objects.

12. The spherical test body of claim 11, wherein one or more of said test objects are removable.

13. The spherical test body of claim 11, wherein at least one of said test objects is adapted for testing the capability of said apparatus to differentiate between objects at different contrast levels.

14. The spherical test body of claim 13, wherein said test object comprises one or more test element bodies formed of material having a predetermined energy absorption characteristic based on physical characteristics, said test element bodies having different absorption characteristics.

15. The spherical test body of claim 2, wherein said test element bodies comprise cylinder-shaped bodies.

16. The spherical test body of claim 11, wherein at least one of said test objects is adapted for testing volume contrast sensitivity of said apparatus.

17. The spherical test body of claim 16, wherein said test object comprises a plurality of voids positioned within a plate.

18. The spherical test body of claim 17, wherein said internally positioned voids are cylinder shaped and have differing diameters and depths.

19. The spherical test body of claim 11, wherein at least one of said test objects is adapted to detect the fidelity of the apparatus in reconstructing an image.

20. The spherical test body of claim 19, wherein said test object comprises channels on an outer surface of said cube.

21. The spherical test body of claim 20, wherein said channels traverse said four walls, said top surface, and said bottom surface.

22. The spherical test body of claim 11, wherein at least one of said test objects is adapted for testing the resolution of the apparatus.

23. The spherical test body of claim 22, wherein said test object comprises line pairs, said line pairs being of predetermined width.

24. The spherical test body of claim 23 wherein the number of line pairs per unit length varies in the direction of scoring.

25. The spherical test body of claim 1, wherein said spherical test body is filled with a fluid.

26. The spherical test body of claim 25, wherein said liquid comprises a copper sulfate solution.

27. The spherical test body of claim 1 further comprising means for providing a fluid bath and for receiving a sample specimen within said bath.

28. A method of determining the operating characteristics of an apparatus used to reconstruct an image of the interior of a subject across a plane, said method using a spherical test body, said spherical test body comprising a hollow spherical first housing positionable within said apparatus, a second housing, means for positioning said second housing within said spherical first housing, and means for determining said operating characteristics, said means for determining said operating characteristics positioned within said second housing, said method comprising the steps of:

positioning said spherical test body within said apparatus; operating said apparatus so as to create an image from said means for determining said operating characteristics; and comparing said image to a predetermined image created by said means for determining said operating characteristics, so as to determine the operating characteristics of said apparatus.

29. The method of claim 28, wherein said apparatus comprises a CAT scanner.

30. The method of claim 28, wherein said apparatus comprises a magnetic resonance imaging system.

31. The method of claim 28, wherein said apparatus comprises an emission computed tomography scanner.

* * * * *

UNITED STATES PATENT AND TRADEMARK OFFICE
CERTIFICATE OF CORRECTION

PATENT NO. : 5,165,050

DATED : November 17, 1992

INVENTOR(S) : David J. Goodenough
Joshua R. Levy

It is certified that error appears in the above-identified patent and that said Letters Patent is hereby corrected as shown below:

Column 8:
In claim 15, line 1, change "2" to --14--.

Signed and Sealed this

Twenty-sixth Day of October, 1993

Attest:

BRUCE LEHMAN

Attesting Officer

Commissioner of Patents and Trademarks